United States Patent
Singaram et al.

(10) Patent No.: US 10,488,418 B2
(45) Date of Patent: Nov. 26, 2019

(54) FLUORESCENCE ASSAY FOR INTESTINAL PERMEABILITY

(71) Applicant: THE REGENTS OF THE UNIVERSITY OF CALIFORNIA, Oakland, CA (US)

(72) Inventors: Bakthan Singaram, Oakland, CA (US); Angel Resendez, Oakland, CA (US); Dominic Luc Webb, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 236 days.

(21) Appl. No.: 15/508,458

(22) PCT Filed: Sep. 2, 2015

(86) PCT No.: PCT/US2015/048203
§ 371 (c)(1),
(2) Date: Mar. 2, 2017

(87) PCT Pub. No.: WO2016/036887
PCT Pub. Date: Mar. 10, 2016

(65) Prior Publication Data
US 2017/0285038 A1  Oct. 5, 2017

Related U.S. Application Data

(60) Provisional application No. 62/044,648, filed on Sep. 2, 2014.

(51) Int. Cl.
| | | |
|---|---|---|
| *G01N 33/58* | (2006.01) | |
| *G01N 33/53* | (2006.01) | |
| *G01N 33/52* | (2006.01) | |
| *G01N 33/493* | (2006.01) | |
| *G01N 21/64* | (2006.01) | |

(52) U.S. Cl.
CPC ....... *G01N 33/582* (2013.01); *G01N 21/6428* (2013.01); *G01N 33/5308* (2013.01); *G01N 21/6486* (2013.01); *G01N 33/493* (2013.01); *G01N 33/52* (2013.01); *G01N 2400/00* (2013.01); *G01N 2458/00* (2013.01); *Y10T 436/143333* (2015.01)

(58) Field of Classification Search
CPC .......... G01N 2400/00; G01N 2458/00; G01N 33/493; G01N 33/5308; G01N 33/582; G01N 33/52; G01N 21/64; G01N 21/6428; G01N 21/6486; Y10T 436/143333

USPC .................. 436/63, 94, 164, 172; 422/82.08
See application file for complete search history.

(56) References Cited

U.S. PATENT DOCUMENTS

| 6,051,260 A | 4/2000 | Liska et al. |
|---|---|---|
| 8,951,503 B2 * | 2/2015 | Singaram ................ B82Y 5/00 424/1.11 |
| 2009/0018418 A1 * | 1/2009 | Markle .............. A61B 5/14532 600/317 |
| 2014/0147856 A1 | 5/2014 | Forsyth et al. |
| 2017/0184574 A1 * | 6/2017 | Singaram ................ C07F 5/025 |

FOREIGN PATENT DOCUMENTS

WO    2013003812    1/2013

OTHER PUBLICATIONS

Resendez et al. Abstract Su1875 from Gastroenterology, vol. 146, issue 5, supplement 1, S-1-S-1099, p. S-491, May 2014.*
International Search Report and Written Opinion issued in PCT/US2015/048203 dated Dec. 4, 2015 (10 Pages).
Camara et al., "Boronic acid substituted viologen based optical sugar sensors: modulated quenching with viologen as a method for monosaccharide detection", Tetrahedron Letters, 43:1139-1141 (2002).
Dicesare et al., "Saccharide Detection Based on the Amplified Fluorescence Quenching of a Water-Soluble Poly(phenylene ethynylene) by a Boronic Acid Functionalized Benzyl Viologen Derivative", Langmuir, 18:7785-7787 (2002).
Miki et al., "Rapid and simultaneous quantification of rhamnose, mannitol, and lactulose in urine by HPLC for estimating intestinal permeability in pediatric practice", Clin Chem Jan. 1996;42(1):71-5.
Resendez et al., "Rapid small intestinal permeability assay based on riboflavin and lactulose detected by bis-boronic acid appended benzyl viologens", Clin Chim Acta. Jan. 15, 2015;439:115-21. doi: 10.1016/j.cca.2014.09.031. Epub Oct. 6, 2014.

* cited by examiner

*Primary Examiner* — Maureen Wallenhorst
(74) *Attorney, Agent, or Firm* — Kilpatrick Townsend & Stockton LLP

(57) ABSTRACT

Provided is a method for quantifying sugar appearing in a biological fluid of a subject, the method include (a) obtaining a biological sample from a subject, who has ingested one or more sugars, over a period of 0 to 24 hours after the ingesting; and (b) measuring the amount of the one or more sugars in the biological sample with an organoborane compound coupled to a fluorophore. Also provided are assays and kits for performing the above methods.

6 Claims, 7 Drawing Sheets

FLUORESCENCE ASSAY FOR INTESTINAL PERMEABILITY

RELATED APPLICATIONS

This application is filed under 35 U.S.C. § 371 as the U.S. national phase of International Application PCT/US2015/048203, filed Sep. 2, 2015, which designated the U.S. and claims priority to the U.S. Provisional Application Ser. No. 62/044,648, filed on Sep. 2, 2014, by Singaram et al., and entitled "FLUORESCENCE ASSAY FOR INTESTINAL PERMEABILITY". The entire disclosure of both applications, including any drawings, is hereby incorporated herein by reference.

FIELD OF THE INVENTION

The present invention is in the field of intestinal permeability and methods of measurement therefor.

BACKGROUND OF THE DISCLOSURE

The small intestine has the dual function of being an absorptive organ as well as a barrier to permeation of toxic compounds and macromolecules. Systemic problems result if either of these functions is disrupted. Increased permeability of the intestinal mucosal barrier correlates with a number of common medical disorders, while decreased permeability appears as a fundamental cause of malnutrition, malabsorption, and failure to thrive. Changes in gut permeability are seen in disorders such as inflammatory bowel disease, Crohn's disease, inflammatory joint disease, food allergy, celiac disease, rheumatoid arthritis, ankylosing spondylitis, Reiter's syndrome, chronic dermatological conditions, schizophrenia, irritable bowel syndrome, allergic disorders, type 1 and type 2 diabetes mellitus, obesity, cancer, environmental enteropathy, autism spectrum disorders and Parkinson's disease. Measurement and manipulation of intestinal permeability is of interest in chemotherapy, disease and treatment monitoring and also drug safety.

Current assessment of small intestinal permeability typically involves oral ingestion of sugar markers such as lactulose and mannitol, followed by collection of urine for 6 hours. The amount of lactulose and mannitol excreted into urine is then measured using HPLC separation coupled to a detector such as a mass spectrometer or evaporative light scatter detector. Alternatively, NADPH-coupled enzyme assays are used. Both methods require considerable time and cost. Currently available technology does not allow rapid, direct quantification of the sugar markers because neither lactulose nor mannitol has intrinsic absorbance or fluorescence.

Thus, a need exists to simplify the measurement and increase throughput of intestinal permeability while lowering the cost per sample.

SUMMARY OF THE INVENTION

The present disclosure relates to a method for quantifying sugar appearing in a biological fluid of a subject, the method comprising: (a) obtaining a biological sample from a subject, who has ingested one or more sugars, over a period of 0 to 24 hours after the ingesting; and (b) measuring the amount of the one or more sugars in the biological sample with an organoborane compound coupled to a fluorophore. Disclosed are also assays and kits for performing the above methods.

DETAILED DESCRIPTION OF THE EMBODIMENTS

Figure 1A:
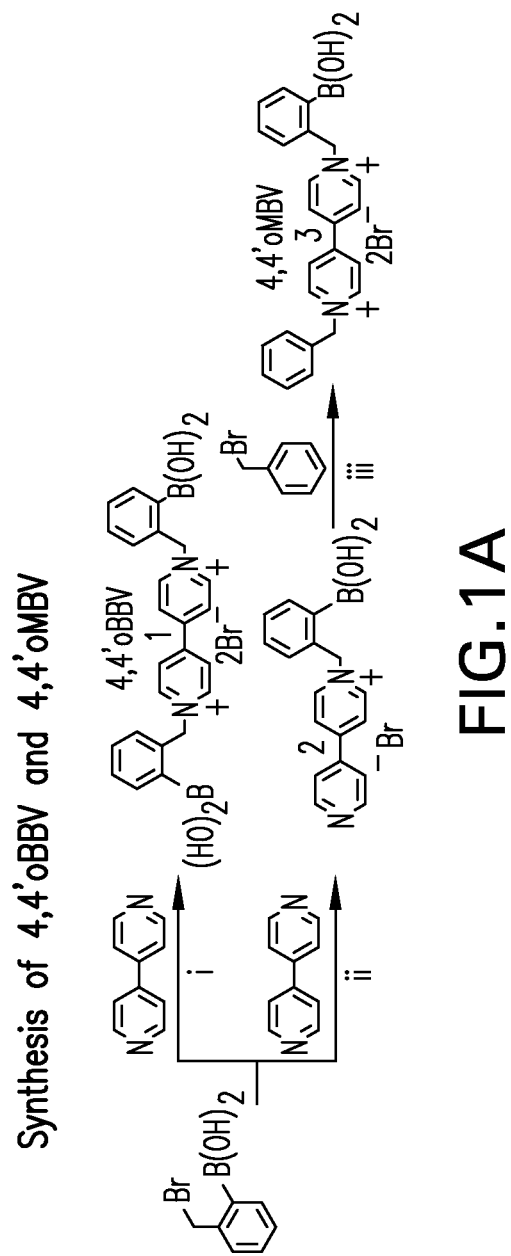
FIG. 1 illustrates a) the synthesis of organoborane sugar sensors, and b) the principle of fluorescence assay for urine lactulose or mannitol.

The terminology used herein is for the purpose of describing particular embodiments only and is not intended to be limiting of the invention. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within one or more than one standard deviation, per the practice in the art. Alternatively, "about" can mean a range of up to 20%, of a given value. Where particular values are described in the application and claims, unless otherwise stated the term "about" meaning within an acceptable error range for the particular value should be assumed.

Unless otherwise defined, all technical and scientific terms used herein have the same meaning as commonly understood by one of ordinary skill in the art to which this invention belongs.

Unless otherwise stated, the following terms used in this application, including the specification and claims, have definitions given below.

The term "sugar" as used herein contemplates a short chain, water-soluble carbohydrate. Sugar may be a monosaccharide, a disaccharide, or an oligosaccharide. The sugar may be naturally occurring or synthetically prepared in the laboratory. In some embodiments the sugar is digestible, while in other embodiments the sugar is non-digestible. The term "sugar" also includes sugar alcohols. As used herein, the term "sugar alcohol" is defined as a polyhydric alcohol (also known as a polyol) formed by the reduction of the carbonyl group of a sugar to a hydroxyl group, with no more than one hydroxy group being attached to any one carbon atom of the sugar alcohol. Examples of sugar alcohols include, but are not limited to, mannitol, sorbitol and xylitol.

The term "subject" as used herein, refers to an animal, preferably a mammal, most preferably a human, who is in the need of assessment of intestinal permeability. In some embodiments, the intestinal permeability may be small intestinal permeability. In some embodiments, the term subject is used interchangeably with the term patient.

The term "biological sample" as used herein, refers to a sample obtained from a subject. The term "biological fluid" as used herein contemplates a liquid biological sample with biomolecules, bioparticles, blood, sweat, saliva, amniotic fluid, lacrimal fluid, urine, milk, mucus, pus, semen, cerebrospinal fluid, vaginal fluid, and combinations thereof. Examples of biomolecules are, but not limited to, nucleic acids, peptides, and enzymes. Examples of bioparticles are, but not limited to, cells, organelles etc.

The term "organoboron" or "organoboronic" or "organoborane" as used herein refers to boron containing organic compounds that possess one or more alkyl, aryl, heteroalkyl, or heretoaryl substituents. The term "organoboronic acid" contemplates boron containing organic compounds that possess one alkyl, aryl, heteroalkyl, or heretoaryl substituent, and two hydroxyl groups. The term "organoborinic acid" contemplates boron containing organic compounds that possess two alkyl, aryl, heteroalkyl, or heteroaryl substituents, and one hydroxyl group.

The term 4,4'oBBV refers to bis-boronic acid viologen 1,1'-bis(2-boronobenzyl)-4,4'-bipyridinium12.

The term 4,4'oMBV refers to mono-boronic acid viologen 1-(2-boronobenzyl)-1'-benzyl-4,4'-bipyridinium.

The term "alkyl" as used herein contemplates substituted or unsubstituted, straight and branched chain alkyl radicals containing from one to fifteen carbon atoms. The term "lower alkyl" as used herein contemplates both straight and branched chain alkyl radicals containing from one to six carbon atoms and includes methyl, ethyl, propyl, isopropyl, butyl, isobutyl, tert-butyl and the like. The alkyl group may be optionally substituted with one or more substituents selected from halogen, —CN, —NO$_2$, —C(O)$_2$R, —C(O)R, —OR, —N($R^N$)$_2$, —N($R^N$)C(O)R, —N($R^N$)S(O)$_2$R, —SR, —C(O)N($R^N$)$_2$, —OC(O)R, —OC(O)N($R^N$)$_2$, —SOR, —SO$_2$R, —SO$_3$R, —S(O)$_2$N($R^N$)$_2$, phosphate, phosphonate, cycloalkyl, cycloalkenyl, aryl and heteroaryl, where $R^N$ is a substituent bonded to a nitrogen.

The terms "aryl," "aromatic group" or "aromatic ring" as used herein contemplates substituted or unsubstituted single-ring and multiple aromatic groups (for example, phenyl, pyridyl and pyrazole, etc.) and polycyclic ring systems (naphthyl and quinolinyl, etc.). The polycyclic rings may have two or more rings in which two atoms are common to two adjoining rings (the rings are "fused") wherein at least one of the rings is aromatic, e.g., the other rings can be cycloalkyls, cycloalkenyls, aryl, heterocycles and/or heteroaryls. The aryl group may be optionally substituted with one or more substituents selected from halogen, alkyl, —CN, —NO$_2$, —CO$_2$R, —C(O)R, —OR, —N($R^N$)$_2$, —N($R^N$)C(O)R, —N($R^N$)S(O)$_2$R, —SR, —C(O)N($R^N$)$_2$, —OC(O)R, —OC(O)N($R^N$)$_2$, —SOR, —SO$_2$R, —SO$_3$R, —S(O)$_2$N($R^N$)$_2$, —SiR$_3$, —P(O)R, phosphate, phosphonate, cycloalkyl, cycloalkenyl, aryl and heteroaryl.

The term "heteroalkyl" as used herein contemplates an alkyl with one or more heteroatoms.

The term "heteroatom" refers to N, O and S.

The term "heteroaryl" contemplates single-ring heteroaromatic groups that may include from one to three heteroatoms, for example, pyrrole, furan, thiophene, imidazole, oxazole, thiazole, triazole, pyrazole, oxodiazole, thiadiazole, pyridine, pyrazine, pyridazine, pyrimidine and the like. The term heteroaryl also includes polycyclic hetero-aromatic systems having two or more rings in which two or more atoms are common to two adjoining rings (the rings are "fused") wherein at least one of the rings is a heteroaryl, e.g., the other rings can be cycloalkyls, cycloalkenyls, aryl, heterocycles and/or heteroaryls. Examples of polycyclic heteroaromatic systems include quinoline, isoquinoline, cinnoline, tetrahydroisoquinoline, quinoxaline, quinazoline, benzimidazole, benzofuran, benzothiophene, benzoxazole, benzothiazole, indazole, purine, benzotriazole, pyrrolepyridine, pyrrazolopyridine and the like. The heterocyclic group may be optionally substituted with one or more substituents selected from the group consisting of halo, alkyl, —CN, —NO$_2$, —CO$_2$R, —C(O)R, —OR, —N($R^N$)$_2$, —N($R^N$)C(O)R, —N($R^N$)S(O)$_2$R, —SR, —C(O)N($R^N$)$_2$, —OC(O)R, —OC(O)N($R^N$)$_2$, —SOR, —SO$_2$R, —SO$_3$R, —S(O)$_2$N($R^N$)$_2$, —SiR$_3$, —P(O)R, phosphate, phosphonate, cycloalkyl, cycloalkenyl, aryl and heteroaryl.

The term "fluorophore" as used herein contemplates a fluorescent chemical compound that can re-emit light upon light excitation. Examples of fluorophore include, but are not limited to, 8-hydroxy-1,3,6-pyrenetrisulfonic acid (HPTS) and 8-methoxypyrene-1,3,6-trisulfonic acid (MPTS). In one embodiment, fluorophore refers to HPTS.

The terms "4× premix buffer," "4× premix," "4× buffer," or "4×" as used herein contemplates a buffer comprising 100 mM 4-(2-hydroxythyl)piperazine-1-ethanesulfonic acid (HEPES), 100 mM sodium phosphate and 0.04% w/v Triton X-100 (or alternatively, polyethylene glycol sorbitan monolaurate) at pH 7.4.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

In one aspect described herein is a method for quantifying sugar appearing in a biological fluid of a subject, the method comprising (a) obtaining a biological sample from a subject, who has ingested one or more sugars, over a period of 0 to 24 hours after the ingesting; and (b) measuring the amount of one or more sugars in the biological sample with an organoborane compound coupled to a fluorophore.

In some embodiments, disclosed herein, one or more sugar is artificial. In some embodiments, one or more sugar is non-digestible. In some embodiments, one sugar is lactulose. In some embodiments, one sugar is mannitol. In some embodiments, the subject ingests two sugars. In some embodiments, the two sugars ingested are lactulose and mannitol.

Figure 4:
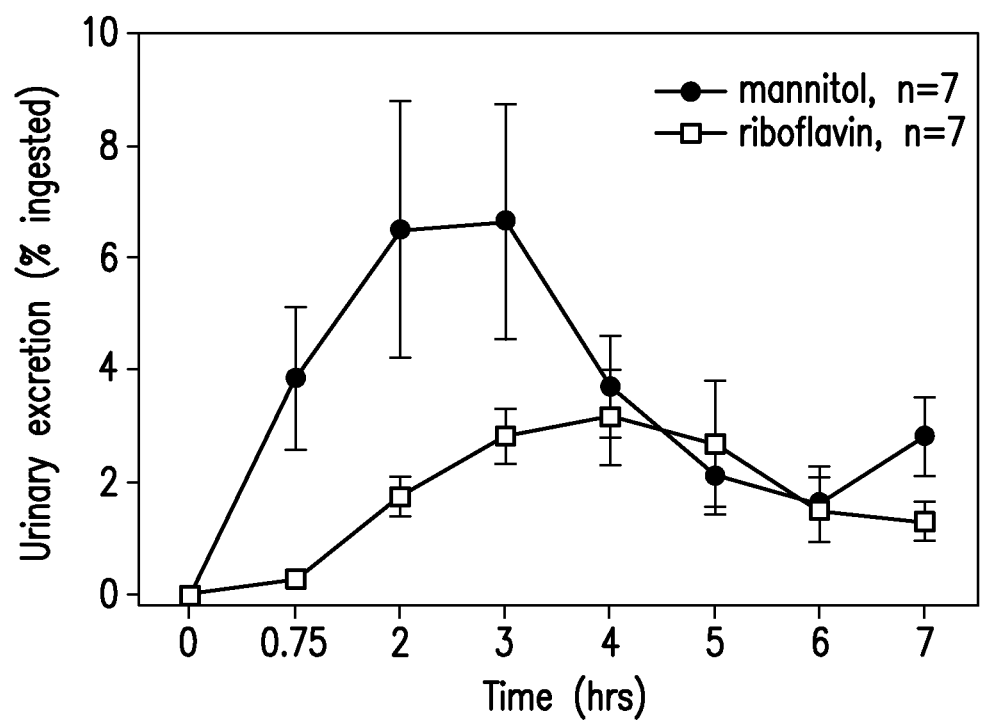
FIG. 4 illustrates temporal measurement of mannitol and riboflavin in healthy human volunteers. Mannitol was measured using 4,4'oBBV and riboflavin by auto-fluorescence (450/580 nm). All data points are mean±SEM.

In some embodiments, riboflavin, reflecting transcellular absorptive capacity of villi, replaces mannitol. In some embodiments, riboflavin values in healthy subjects varies less than mannitol. In some embodiments, the delay in appearance of riboflavin relative mannitol reflects differences in where the initial uptake occurs. In some embodiments, riboflavin is confined to uptake through the Riboflavin Transporter 2 (RFT2) and correlates more strongly with condition of villi tips of duodenum and jejunum. In some embodiments, wherein RFT2 transport is down-regulated in gastrointestinal diseases, riboflavin measurements serve to identify such conditions. In some embodiments, the time delay in appearance of riboflavin in the biological sample relative to mannitol reflects differences in where the initial uptake occurs. Referring to FIG. 4, in some embodiments, the range in riboflavin values suggests a narrow range of values in healthy individuals.

In some embodiments, the organoborane compound is organoboronic acid. In some embodiments, the organoboronic acid is a boronic acid viologen. In some embodiments, the boronic acid viologen is bis-boronic acid viologen 1,1'-bis(2-boronobenzyl)-4,4'-bipyridinium (4,4'oBBV). In some embodiments, the boronic acid viologen is mono-boronic acid viologen 1-(2-boronobenzyl)-1'-benzyl-4,4'-bipyridinium (4,4'oMBV). Referring to FIG. 3, it is noted that 4,4'oMBV is a less potent quencher than 4,4'oBBV, requiring about 20% higher concentration to achieve the same extent of quenching. As sugar concentration increased, 4,4'oBBV showed stronger de-quenching than 4,4'oMBV, indicating 4,4'oBBV had superior ability to resolve different sugar concentrations. In some embodiments, a 4,4'-viologen lacking boronic acids is a weaker quencher compared to 4,4'oBBV and 4,4'oMBV. This means that boronic acids facilitate HPTS quenching and that facilitation is lost when sugars react with boronic acid groups. Two boronic acids provide more facilitation to quenching, and as a result, more capacity to de-quench in the presence of sugar.

In some embodiments, the biological sample is a biological fluid. In some embodiments, the biological fluid is urine. In some embodiments, the urine sample is collected from the subject at regular intervals after ingestion of the sugar and/or riboflavin. In some embodiments, the urine sample is collected for 3, 6, 9, 12, 18, 24 hours, or any other time in between, at regular intervals after ingestion of the sugar and/or riboflavin.

In another aspect, disclosed herein is a fluorescence assay kit comprising a solution of an organoborane compound, a fluorophore, 4-(2-hydroxyethyl)-piperazine-1-ethanesulfonic acid (HEPES), sodium phosphate, and Triton X-100, wherein the solution is distributed into one or more microtiter plates. The term "microtiter plate" as used herein refers to a flat plate with multiple wells used as small test tubes. Examples of the number of wells include, but are not limited to, 6, 24, 96, 384, 1536, 3456, or 9600 wells. In one embodiment, the volume of this reagent solution prior to addition of biological fluid in each well is 10 μL.

In some embodiments, the microtiter plates are covered with adhesive tape. In certain embodiments, the fluorescence assay kit is stored at between 2° C. and 15° C., most preferably at 4° C. In one embodiment, the kit comprises a solution with 1.6 mM 4,4'oBBV or 2.0 mM 4,4'oMBV, 16 μM HPTS, 100 mM 4-(2-hydroxyethyl)piperazine-1-ethanesulfonic acid (HEPES), 100 mM sodium phosphate, and 0.04% w/v Triton X-100 at pH 7.4.

In some embodiments, the fluorescence assay kit further comprises a buffer solution for blank subtraction. In some embodiments, the buffer solution comprises HEPES, sodium phosphate and Triton X-100. In one embodiment, the buffer solution comprises the 4× premix buffer. In some embodiments, the buffer solution further comprises a fluorophore. In some embodiments, the buffer solution further comprises a fluorescence quencher. In some embodiments, the fluorescence quencher is 4,4'oBBV or 4,4'oMBV. In other embodiments, the quencher is a compound selected from the group consisting of the following structures:

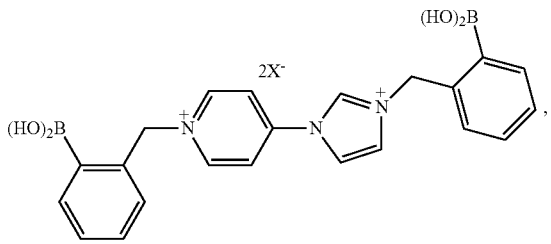

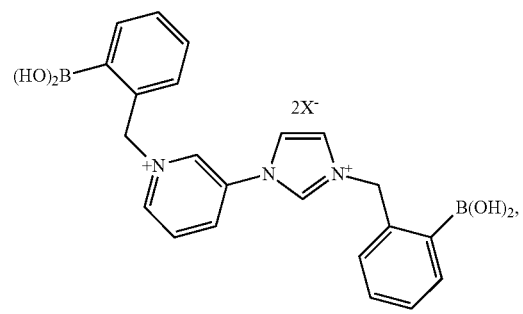

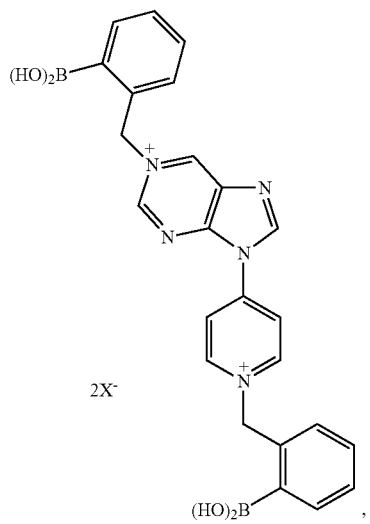

-continued
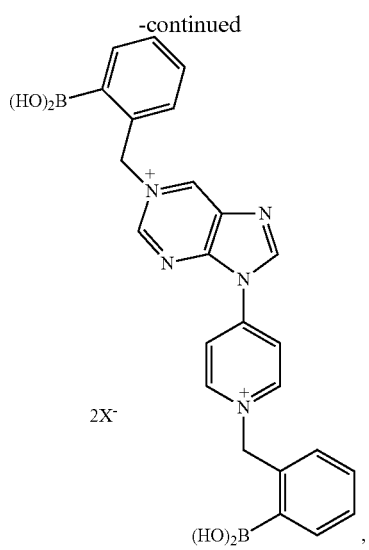
2X⁻
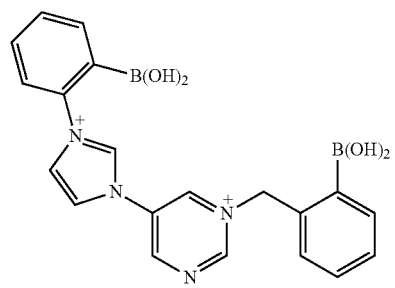
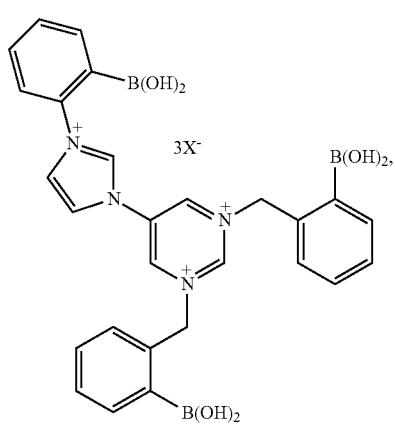
3X⁻
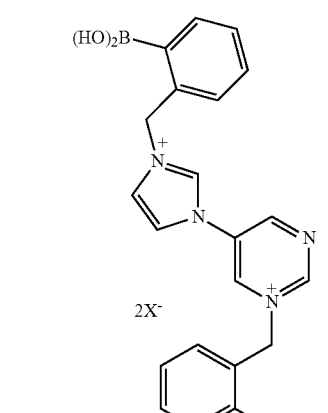
2X⁻
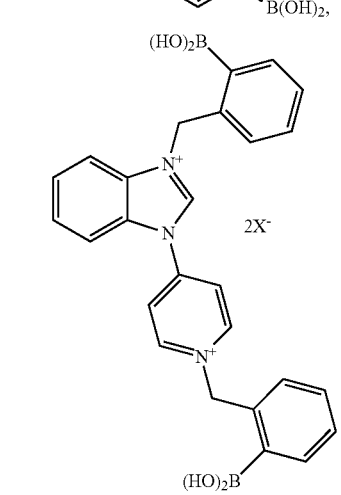
2X⁻

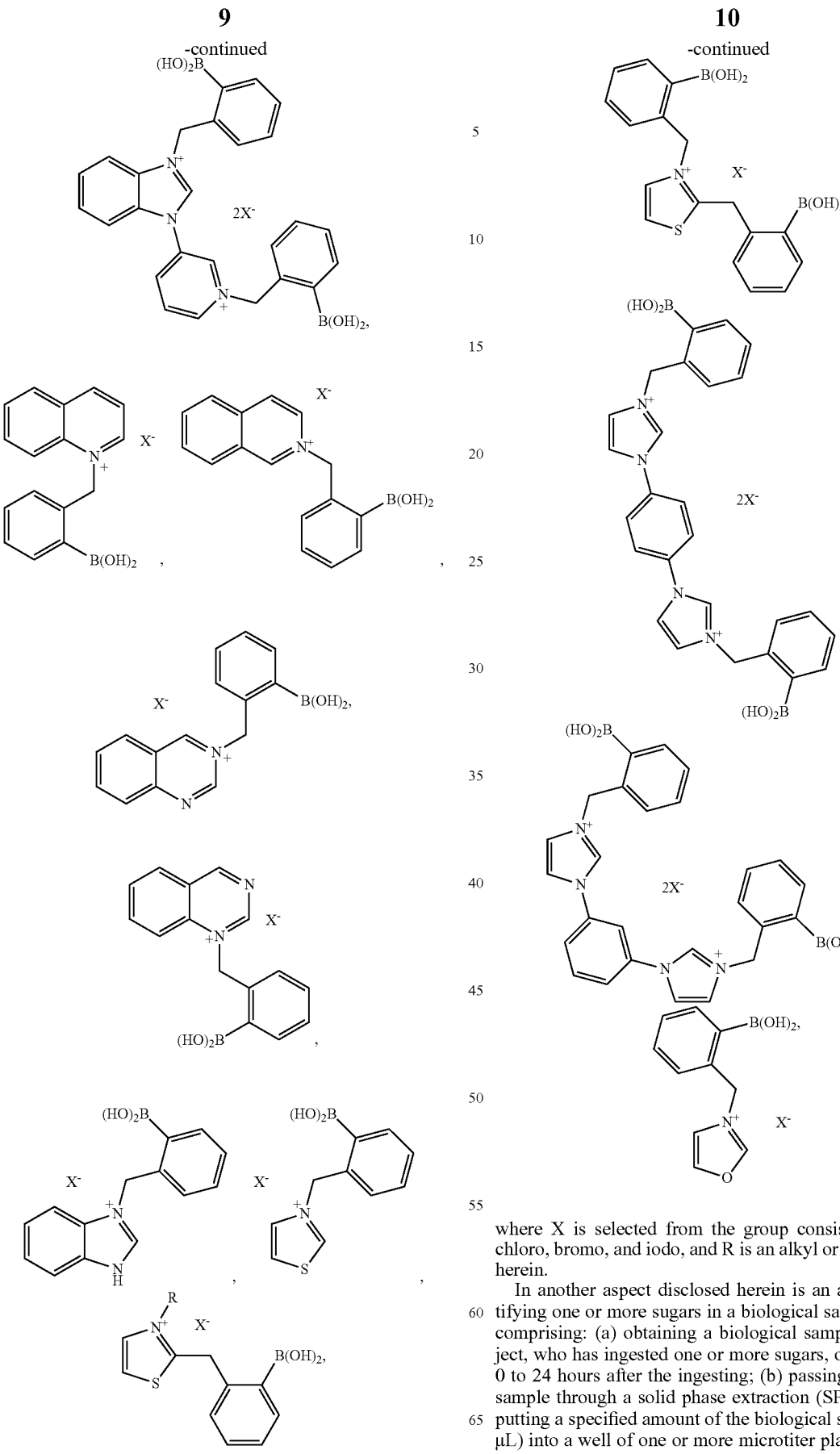

where X is selected from the group consisting of fluoro, chloro, bromo, and iodo, and R is an alkyl or aryl, as defined herein.

In another aspect disclosed herein is an assay for quantifying one or more sugars in a biological sample, the assay comprising: (a) obtaining a biological sample from a subject, who has ingested one or more sugars, over a period of 0 to 24 hours after the ingesting; (b) passing the biological sample through a solid phase extraction (SPE) column; (c) putting a specified amount of the biological sample (e.g., 30 µL) into a well of one or more microtiter plates, the well of the microtiter plate further comprising a solution of an organoboronic acid, a fluorophore, 4-(2-hyrozyethyl)piperazine-1-ethanesulfonic acid, sodium phosphate, and polyethylene glycol sorbitan monolaurete (e.g., 10 μL); (d) centrifuging the one or more microtiter plates containing the biological sample; (e) measuring the fluorescence of the biological sample solution in the well of the one or more microtiter plates; and (f) determining the amount of one or more sugars in the biological sample from the fluorescence in the sample.

In some embodiments, the subject ingests riboflavin at the same time as ingesting the one or more sugars. In some embodiments, the measurement of the amount of sugar in the biological sample is normalized against riboflavin fluorescence in the same sample. In some embodiments, the subject ingests riboflavin, lactulose and mannitol simultaneously. In some embodiments, the lactulose/riboflavin or mannitol/riboflavin ratio in the biological sample is used to determine the relationship between paracellular (lactulose) or non-specific transcellular (mannitol) intestinal absorption and the highly selective and rapid transport of riboflavin. In some embodiments, the time delay in appearance of riboflavin in the biological sample relative to mannitol reflects differences in where the initial uptake occurs. In some embodiments, the subject ingests riboflavin and two sugars. In some embodiments, the two sugars are lactulose and mannitol.

In some embodiments, riboflavin in the urine is assayed by autofluorescence before it is passed through the solid phase extraction (SPE) column. In some embodiments, riboflavin is removed by the SPE column. In some embodiments, the SPE column is a reverse phase column. In some embodiments, the SPE column is a C18 column. In one embodiment, the C18 column is a 3 cc 500 mg C18 solid phase extraction column. The process of passing the biological sample, such as urine, through a SPE column removes riboflavin and endogenous fluorescence such that it cannot interfere with lactulose or mannitol measurements.

Currently available methods for performing light based assays on urine presents the concerns of interfering absorbance and fluorescence. For viologen assay samples, the C18 SPE cleanup eliminates riboflavin and endogenous fluorescence to the extent of being negligible. When high throughput is desired, 96 or 384 well filter plates loaded with C18 is used with a plate centrifuge.

In some embodiments, the fluorophore is HPTS. In some embodiments, the fluorophore is MPTS.

In some embodiments, the urine is transferred into the microtiter plate, which comprises a solution of 4,4'oBBV or 4,4'oMBV, fluorophore, HEPES, sodium phosphate, and Triton X-100. In some embodiments, the microtiter plate also contains lactulose or mannitol standards.

In some embodiments, the microtiter plate containing the biological sample is centrifuged. In one embodiment, the plate is centrifuged at 2500 relative centrifugal force (RCF) for 10 minutes at room temperature. This step is crucial in order to segregate unreacted quencher-dye complex, which has strong interfering optical absorbance and poor solubility.

Figure 2A:
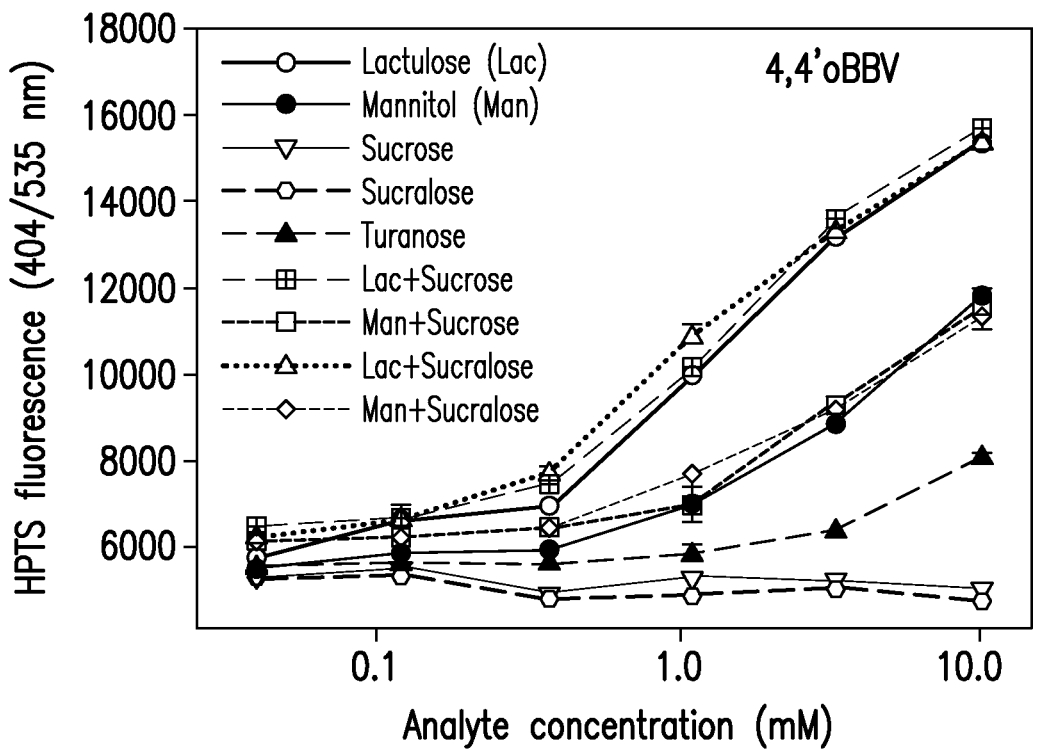
FIG. 2 illustrates concentration dependencies of the viologen based assay with human urine. (a) Standard curves for lactulose and mannitol using 4,4'oBBV demonstrate strongest sensitivity to lactulose and strong discrimination against sucrose and sucralose. (b) Corresponding standard curves for 4,4'oMBV showing similar pattern of responses albeit with weaker changes in fluorescence. (c) Auxiliary data showing comparatively stronger sensitivity for fructose over galactose, the two moieties of lactulose. This assay system lacks sensitivity for glucose and lactose, which can appear in some patient urine samples. (d) Corresponding data for 4,4'oMBV. Data points are mean±SEM, n=3.
Figure 2B:
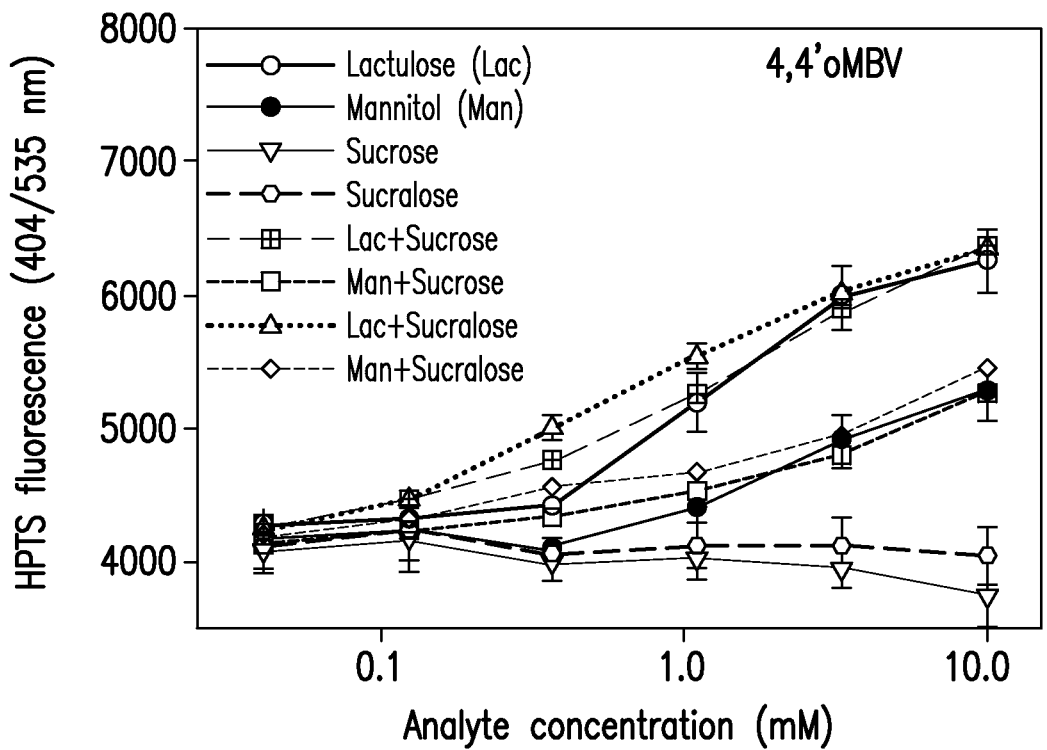
Figure 2C:
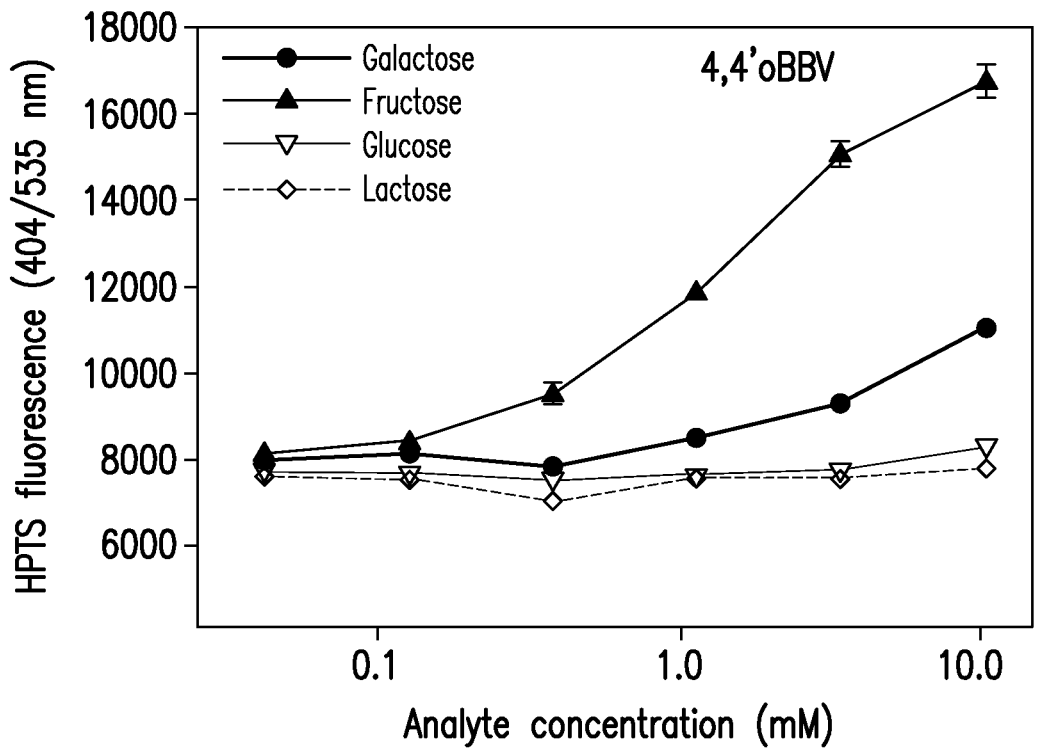
Figure 2D:
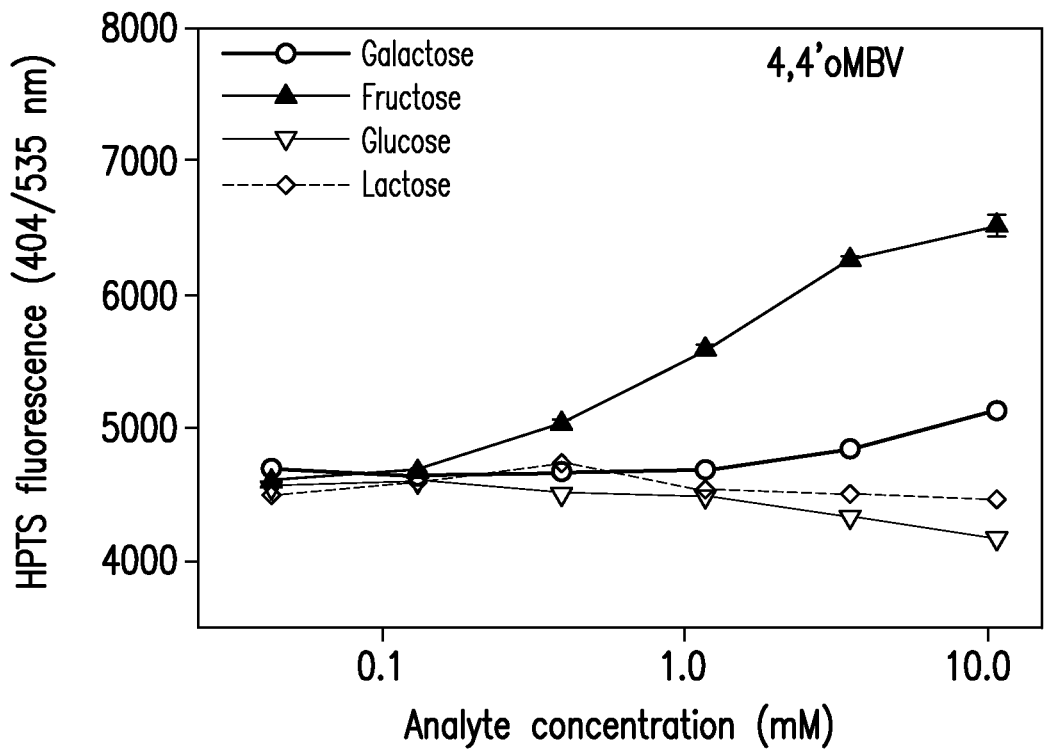

Referring to FIG. 2(b), it is noted that the upward trend in signal intensity is parallel across all sugar concentrations with rising temperature. This trend was seen with other sugars and with 4,4'oMBV. Thus, solubility does not increase with temperature. In one embodiment, the assay is performed in room temperature. The problem of limited solubility of 4,4'oBBV-HPTS was solved by centrifuging the plate and reading fluorescence from the top of the solution.

In some embodiments, a microtiter plate reader is configured to read from the top of the solution to preferentially obtain fluorescence from free, unquenched fluorophore. In some embodiments, fluorescence is determined at Exc/Em 405/535 nm for HPTS or 404/436 nm for MPTS. In one embodiment, Tecan Infinite M200 plate reader (Tecan Group Ag, Mannedorf, Switzerland) is used. In another embodiment, a fluorescence spectrophotometer may be used with a cuvette to obtain the fluorescence.

In some embodiments, to measure riboflavin, 100 μL urine is placed into 900 μL ethanol, vortexed and centrifuged at 2500 RCF for 10 minutes at 4° C. Then, 40 μl of the supernatant is placed in an empty microtiter plate (Corning 3694). The intrinsic fluorescence of riboflavin is measured at Exc/Em 450/580 nm.

In some embodiments, blanks are subtracted and a curve fit is made to derive an equation to calculate concentrations. A number of equations may be used to calculate concentrations. In one embodiment, a four parameter sigmoidal curve fit is used. Once concentrations are determined in units of g/mL, they are multiplied by the total volume in mL of urine collected, giving the total grams of one or more sugars in the urine sample. This is then divided by the grams ingested and multiplied by 100 to yield the percent ingested. When included in the assay, riboflavin, also transformed to percent ingested, may be used to normalize the data, thus arriving at a lactulose/riboflavin or mannitol/riboflavin ratio.

Typical values for humans are as follows: lactulose, 0.2-1.5 mM; mannitol 1-10 mM; riboflavin, 0.01-0.1 mM. Values are generally above the detection limit for each analyte. Detection limit is defined as the analyte concentration in the original urine sample at which fluorescence exceeds the background level plus 3 times the standard deviation of the background. Beyond the simplicity of employing riboflavin, the variation between healthy individuals, as measured by the standard deviation, is typically around 12% lower than for mannitol.

In another aspect, described herein is a method of screening new drugs in a subject for adverse effects in a small intestine, the method comprising: (a) obtaining a biological sample from a subject, who has ingested one or more sugars, over a period of 0 to 24 hours after ingestion; (b) obtaining a second biological sample from the subject, who has ingested a new drug and one or more sugars, over a period of 0 to 24 hours after ingestion; (c) measuring the amount of the one or more sugars in the two biological samples with an organoboronic compound coupled to a fluorophore; and (d) comparing the amount of the one or more sugars in the biological samples to determine if the new drug resulted in increased or decreased small intestinal permeability.

Figure 3A:
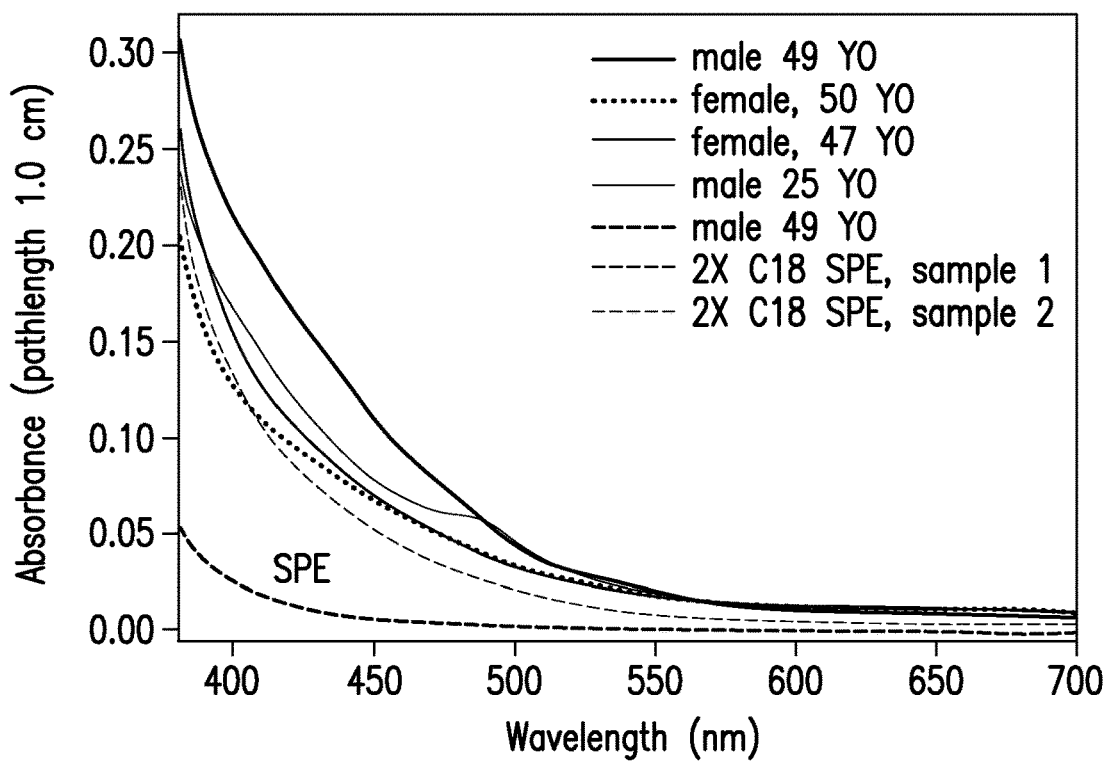
FIG. 3 illustrates a) typical absorbance spectra from 5 human volunteers at the time of permeability test. Due to strong spectral overlap, the result of solid phase extraction (SPE) is only shown for the first two subjects, the first having the highest absorbance obtained in this study. b) Temperature dependency of viologen based fluorescence assay. Magnitude of increase in fluorescence is relatively constant across the temperature range 10-50° C. Some of the signal increase is an intrinsic property of HPTS, as seen with 4 µM HPTS in the absence of viologen (dark blue diamond with highest signal). In the absence of sugar at or below 5° C., signal dips below blank values, due to absorbance in presence of weaker fluorescence. Data points are mean±SEM, n=6.
Figure 3B:
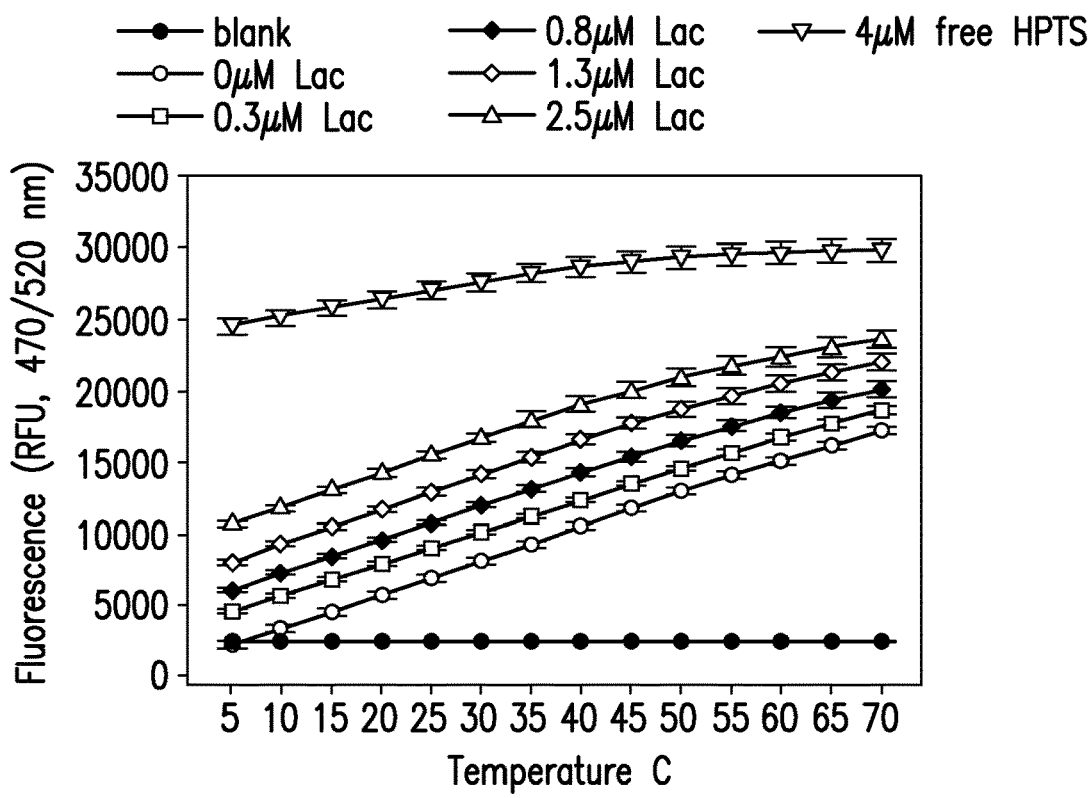

In some embodiments, sucrose and sucralose are present in the permeability test to assess gastroduodenal and colon permeability. Neither sucrose nor sucralose interfere with the viologen based method (FIGS. 3A and 3B). Therefore, their inclusion in clinical studies is not an impediment to the presently disclosed permeability assay. Furthermore, presence of glucose or lactose in the urine does not complicate this assay because 4,4'oBBV gave essentially no response to 10 mM glucose or lactose (FIGS. 3C and 3D). Similarly, the mere presence of cis diols is not sufficient to generate a signal.

In one embodiment, a subject taking non steriodal anti-inflammatory drugs (NSAIDs) for chronic pain that developed ulcers had lactulose levels around twofold above the mean of the healthy volunteers. In another embodiment, a type-2 diabetic subject taking NSAIDs had lactulose levels around twofold above the mean of the healthy volunteers. In another embodiment, a subject taking two NSAIDs during the past several years for chronic pain had a high lactulose level and a low riboflavin level. These cases are consistent with increased small intestinal permeability. The latter case further suggested detection of villi tip architectural damage.

At alkaline pH, boronic acids act by reversible formation of cyclic esters with selective cis diols within saccharides. We devised two viologens demonstrating high sensitivity and selectivity for lactulose. The binding mechanism of boronic acids to diols has been investigated for glucose and fructose. $^{13}$C-NMR demonstrated that phenylboronic acid forms the β-D-fructofuranose complex or β-D-fructopyranose at C2 and C3 under alkaline conditions similar to this study. Since lactulose contains a fructose moiety in which hydroxyls at C2 and C3 are available, the present viologens were anticipated to interact at these carbons, with galactose potentially contributing a smaller component. Unexpectedly, turanose, a glucose-(1→3)-fructose analog of sucrose differing only in the glycosylic linkage at C3 of fructose, gave ~20% of the lactulose fluorescence, and ~30% of fructose, whereas sucrose gave no signal. Hence, C3 of the fructose moiety likely accounts for most of the boronic acid binding to lactulose in this assay system, but is not absolutely required. Lactulose gave ~20% stronger signal than fructose while equimolar amounts of fructose with galactose gave a higher signal than lactulose. Relative selectivity of 4,4'oBBV was lactulose>fructose>galactose, whereas 4,4'oMBV was similar for lactulose and fructose. Without being bound to a particular theory, lactulose binds 4,4'oBBV in a bidentate (cooperative) fashion involving both the fructose and galactose moieties, explaining the selectivity and sensitivity of this assay for lactulose.

EXAMPLES

Preparation of boronic acid viologens 4,4'oBBV and 4,4'oMBV: The reaction scheme with compound numbering are shown in FIG. 1(a). Synthesis of 4,4'oBBV was as described in Camara J. N. et al. *Tetrahedron Letters* 2002; 43:1139-1141. For 4,4'oMBV, 2-bromomethylphenyl boronic acid was reacted with excess 4,4'-bipyridyl in acetone to afford the mono-substituted 4,4'bipyridyl adduct (compound 2). Combining excess compound 2 with benzyl bromide in a solvent mixture of MeCN and MeOH yielded 4,4'oMBV (compound 3) after precipitation from the reaction mixture with acetone. Reagents and conditions were: (i) dimethylformamide, 55° C., 48 hrs, 90% (compound 1); (ii) acetone, 25° C., 2 hrs, 70% (compound 2); (iii) MeCN, MeOH, 55° C., 24 hrs, 86% (compound 3).

Figure 1B:
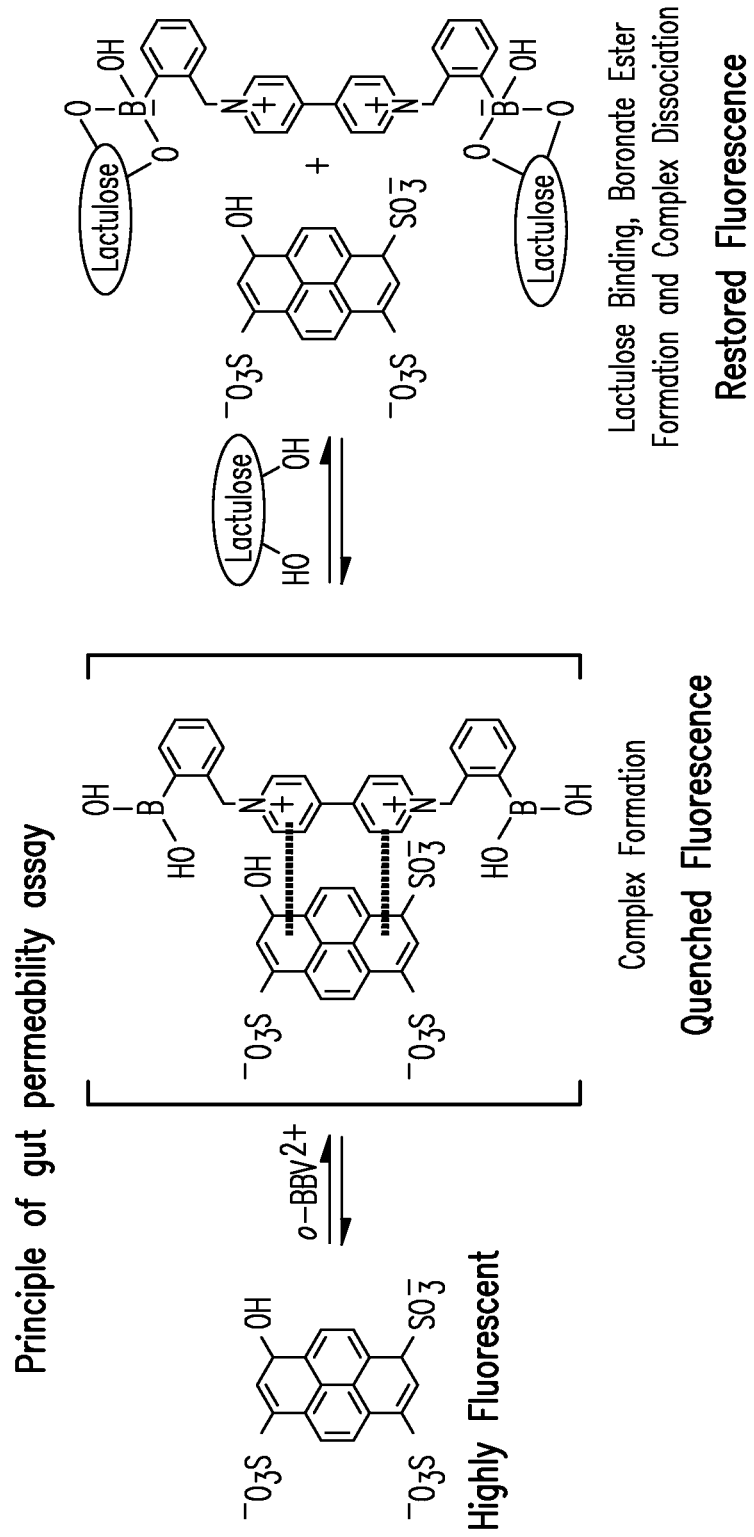

Molecular mechanism behind the organoboron based fluorescent lactulose assay: FIG. 1(b) illustrates a proposed molecular mechanism behind the organoborane based fluorescent lactulose assay. The sensing ensemble is comprised of an anionic fluorophore, 8-hydroxypyrene-1,3,6-trisulfonic acid (HPTS) and a boronic acid-appended viologen (4,4'oBBV or 4,4'oMBV). HPTS forms a weak ground state complex with the cationic viologen sugar receptor, quenching its fluorescence. Ground state complex formation between the anionic fluorophore and cationic viologen sugar receptor facilitates an electron transfer from the fluorophore to the viologen, decreasing fluorescence. In some embodiments, at pH about 7.4, the cationic boronic acid viologen receptor has a high intrinsic affinity for diols, which upon binding, partially neutralizes the charge of the viologen. This is caused by an equilibrium shift from the neutral boronic acid to the anionic boronate ester, lowering its affinity for HPTS, giving increased fluorescence.

Baseline absorbance spectra of urine: Because the assay uses spectroscopic methods, urine samples were evaluated for interfering absorbance. Urine was collected from 5 volunteers, including subjects with suspected gut hyperpermeabilty. They were instructed to drink 0.5-1.0 L water the night before and in the morning about 3 hours prior to sample collection. The first morning urine was voided. No food or additional beverages were consumed until after the baseline sample was collected. This reflects current practice prior to initiating the permeability test. Absorbance was scanned from 380-700 nm at the time of collection. Below 380 nm, samples are essentially opaque. Absorbance is negligible from 700-1100 nm.

Temperature and solubility of reagents: A BioRad C1000 thermal cycler with CyberGreen filters (Exc 470, Em 520 nm) was used to determine the thermal properties of the assay. A smaller set of samples were checked at 420/535 nm on the plate reader normally used for the permeability test. Aliquots of 6 µl of a 4× premix containing 500 µM 4,4'oBBV and 16 µM HPTS in 100 mM sodium phosphate buffer at pH 7.4 were distributed onto PCR plates (HSP-9601, BioRad, Hercules, Calif., USA). Then, 18 µl urine samples containing serially diluted 0 to 80 mM lactulose were distributed into the wells. Plates were sealed with clear plate tape and assayed from 5 to 70° C.

Intestinal permeability test in humans: Subjects consumed 0.5-1.0 L water the night before and in the morning about 3 hour prior to sample collection. The first morning urine was voided. No food or other beverages were consumed prior to the test. Permeability probes were ingested after baseline urine collection. Doses for the permeability probes were 50 mg riboflavin and 5 g mannitol or 10 g lactulose (15 mL at 0.67 g/mL). Test subjects were permitted to drink water or coffee as desired. Light snacks were permitted after the fourth hour. Urine volumes were recorded and 50 mL was retained for analysis. Studies were carried out in Sweden according to ethical approval Dnr 2010/184 held at Uppsala University, Sweden.

Urine Assays

Sample collection: Freshly collected urine (50 ml) was first centrifuged 2500 RCF at 4° C. for 10 minutes. 100 µl supernatant was set aside for riboflavin analysis, the remaining supernatant was frozen at −20° C. for later mannitol or lactulose analyses.

Riboflavin assay: The above 100 µl urine set aside and standards prepared in pooled baseline samples were diluted in 900 µl EtOH, vortexed and centrifuged. Supernatants were pipetted 40 µL/well in duplicate into plates (#3694, Corning, USA). Fluorescence (Exc/Em 450/580 nm) was read on a plate reader (Infinite M200Pro, Tecan, Switzerland). Concentration was calculated as mg/mL and multiplied by total urine volume in mL, giving total mg in urine. The mg in urine/mg ingested×100 yielded % ingested.

C18 solid phase extraction of samples for lactulose and mannitol: To remove riboflavin and other colored components, 2 mL urine was processed twice through solid phase extraction (SPE) using 500 mg C18 columns fitted onto a Waters/Millipore SPE vacuum manifold (max −50 kPa, ~0.5 mL/min). The SPE column was cleaned with MeOH and H2O between runs. Mannitol and lactulose recovery were both ~91%. Data was corrected for a 9% loss. After SPE, samples were directed to the various assays.

Effectiveness of C18 cleanup: FIG. 2a shows the absorbance of a typical range of urine samples as they are received and the effectiveness of C18 solid phase extraction. After 2 cycles of extraction, at which stage no further cleanup can be achieved, urine remained opaque below ~380 nm and negligible above 700 nm. Variation in absorbance between samples is largely removed. This proved adequate for the 405/535 nm wavelengths of HPTS. Background fluorescence was reduced to ~20 times below the bottom of the standard curves.

Viologen method for lactulose and mannitol permeability in humans: Ready-made assay 96 well plates were prepared (#3694, Corning, 199 USA). A 4× premix buffer was prepared (0.1 M sodium phosphate, 0.1 M HEPES, 0.04% Triton X-100, pH 7.4). To this was added HPTS (16 µM) and quencher (1.6 mM 4,4'oBBV or 2.0 mM 4,4'oMBV), each 4 times above final concentration. The different viologen concentrations were chosen to achieve similar extents of quenching in the absence of sugar (about 20% of free fluorophore) while preserving a strong signal to noise (S/N). Blank wells were given 10 µl 4× premix buffer with neither HPTS nor viologen. Some wells received 16 µM HPTS without quencher to determine maximum possible fluorescence. All other wells received 10 µl of the complete 4× premix. Those premixes containing 4,4'oBBV were continuously vortexed because the mixture is a suspension. Plates were sealed with plate tape and stored at 4° C. until use.

Upon running an assay, 30 µl of standards or samples were pipetted into wells. Final concentrations were 4 µM HPTS and 400 µM 4,4'oBBV or 500 µM 4,4'oMBV. Urine samples were placed in both blank wells (for individual sample blanking) and wells containing complete 4× premix. Plates were put on a shaker for 1 hr, RT. During this time, sugars interacted with the HPTS-viologen complex, liberating HPTS into solution. Plates were then centrifuged at 2500 RCF for 10 minutes at room temperature to pull down remaining HPTS-quencher particulate matter. Plate tape was removed and fluorescence read on a plate reader (Tecan M-200 Infinite, gain 70, 404/535 nm). The height was adjusted to read from the top of the solution (18 mm). This wavelength combination is pH insensitive and poorly affected by any residual riboflavin or endogenous fluorophores that might still be present after C18 SPE. A Marquardt 4-parameter curve fit was used. Sugar concentrations were calculated as g/mL and multiplied by total urine volume in mL, giving total amount of urine in grams. Values were corrected for percentage recovery from the C18 SPE step. The g in urine/g ingested×100 yielded % ingested. Lactulose measurements were confirmed by enzyme assay. Mannitol measurements were confirmed by HPLC-Evaporative Light Scattering Detector (HPLC-ELSD) using a C8 pre-column and Prevail Carbohydrate ES 5µ 250×4.6 mm column (Grace Davison 224 Discovery Sciences, Ill., USA) with 80:20 MeCN/H2O.

Statistics: The lower limit of detection (LLOD) was defined as the analyte concentration in the urine sample at which fluorescence intensity in the assay was 3 standard deviations above the mean baseline fluorescence. Similarly, the lower limit of quantification (LLOQ) was defined as 10 standard deviations above the mean baseline fluorescence. Coefficient of variation percent (CV %) was determined by averaging sets of samples each measured in 4 wells. Results are given as mean±SEM.

Temperature and solubility: Temperature and solubility of 4,4'oBBV were evaluated because boronic acid moieties of organoboranes generally confer reduced solubility on organoboranes. In some embodiments, there was a precipitate in the presence of HPTS (dye). In some embodiments, the amount of precipitate was inversely proportional to sugar concentration and HPTS fluorescence.

In some embodiments, solubility increased in the presence of lactulose. In some embodiments, in homogeneous buffer systems, the optimal quencher/dye ratio was 125:1 with 500 µM 4,4'oBBV. In some embodiments, 4,4'oBBV and HPTS was a superior quencher-dye pairing for lactulose measurement.

In some embodiments, following centrifugation, about 90% of HPTS and a similar amount of 4,4'oBBV was trapped in the pellet. When used to assay sugars, the supernatant of the 4× premix performed poorly compared to the re-suspended precipitate due to loss of most of the fluorophore and viologen. The thermal dependency of the combination of 500 µM 4,4'oBBV and 4 µM HPTS (final concentrations) for lactulose standards in urine is illustrated in FIG. 2b. When temperature and sugar concentration were low, HPTS fluorescence approached that of the blank. The absorbance contributed by 4,4'oBBV and quenched HPTS in the absence of fluorescence lead to values below the blank, and yielded negative values after blank subtraction. A final concentration of 4,4'oBBV (400 µM) was therefore chosen for assays, giving higher S/N at low sugar concentrations. After establishing that the precipitate was a component of the assay, the plate was centrifuged prior to reading (2500 RCF, 10 min). The plate reader was then configured to read from the top of the solution, thus removing any influence of residual unreacted precipitate. Separate experiments confirmed this was relevant for the pH insensitive 420/535 nm wavelengths used in an actual permeability test.

Concentration dependencies and selectivity: In one embodiment, FIG. 3 shows standard curves used to determine limits of detection and quantification for lactulose and mannitol as well as comparisons to other sugars. Limits of detection and quantification are tabulated in Table 1. Also shown are concentration ranges and intra-assay CV %.

To illustrate the sensitivity of the assay relative to values obtained in urine samples, the range of concentrations are given instead of percent ingested normally stated in a clinical report. The riboflavin assay was at least two orders of magnitude more sensitive than required using the current 50 mg dose. Because this assay measured intrinsic riboflavin fluorescence, standards were linear. For the viologen based sugar assays, the initial quench (as percent of maximum HPTS fluorescence in absence of viologen) indicated that HPTS fluorescence was strongly quenched at the 0 µM sugar condition at the bottom of the standard curve. This also illustrated that 4,4'oMBV was a less potent quencher than 4,4'oBBV, requiring about 20% higher concentration to achieve the same extent of quenching. As sugar concentration increased, 4,4'oBBV showed stronger de-quenching than 4,4'oMBV, indicating 4,4'oBBV had superior ability to resolve different sugar concentrations. Gut permeability assays therefore used 4,4'oBBV. Given that lactulose absorption was very low in healthy subjects, the lower LLOQ of 4,4'oBBV also made it better suited for the gut permeability test. The low CV % achieved (intra-assay) throughout was afforded by the limited number of pipetting steps.

Table 1 shows the lower limits of detection (LLOD) and quantification (LLOQ), range and CV % for riboflavin, lactulose and mannitol in human urine. The data was obtained from 3 separate runs (3 different occasions) in which all parameters were assayed in parallel. All data points were measured in duplicate on all occasions. Background (assay noise level) and standard deviation for organoboranes were defined as baseline urine with HPTS (404/535 nm) and viologen in the absence of sugar. This 0 µM sugar standard was the point at which maximum HPTS quench was achieved. Values for 4,4'oBBV were averages for two different batches.

TABLE 1

| Parameter | Initial Quench % Max | LLOD μM | LLOQ μM | RANGE μM | CV % |
|---|---|---|---|---|---|
| Riboflavin | N/A | <0.10 | 0.30 | 29.3 ± 6.8 | <5 |
| Lactulose with 4,4'oBBV | 24 | 90 | 364 | 132 ± 59 | 3.3 |
| Lactulose with 4,4'oMBV | 16 | 108 | 704 | | |
| Mannitol with 4,4'oBBV | 24 | 416 | 860 | 3929 ± 972 | 2.4 |
| Mannitol with 4,4'oBBV | 16 | 354 | 1250 | | |

The term "Initial quench" as used herein refers to HPTS fluorescence in presence of quencher and absence of sugar (maximum achievable quench) as a percent of maximum possible fluorescence with 4 μM free HPTS in absence of any quencher. The term "LLOD" as used herein refers to analyte concentration in original urine sample (as opposed to final concentration in the assay) at which the fluorescence signal equals or exceeds 3 standard deviations above mean assay noise level. The term "LLOQ" as used herein refers to analyte concentration in original urine sample at which the fluorescence signal equals or exceeds 10 standard deviations above mean assay noise level. The term "range" as used herein refers to urine concentrations found in healthy volunteers before transforming data to % ingested. The term "Mean±SEM" as used herein refers to standard mean plus or minus standard error of mean as generally understood in medical science. The term "CV %" as used herein refers to intra-assay coefficient of variation for samples.

Temporal overlap of mannitol and riboflavin: In one embodiment, FIG. 4 shows temporal appearance of riboflavin and mannitol in urine when sampled hourly after ingestion. Riboflavin consistently appeared somewhat later than mannitol. Both riboflavin and mannitol returned to baseline at about 6 hours, demonstrating that 6 hours was an acceptable cutoff for studies of small intestinal permeability. Thus, riboflavin, a true nutrient absorbed by way of transport through RFT2, is able to replace mannitol, which was used as a surrogate marker for nutrient malabsorption, as in active celiac disease.

Figure 5:
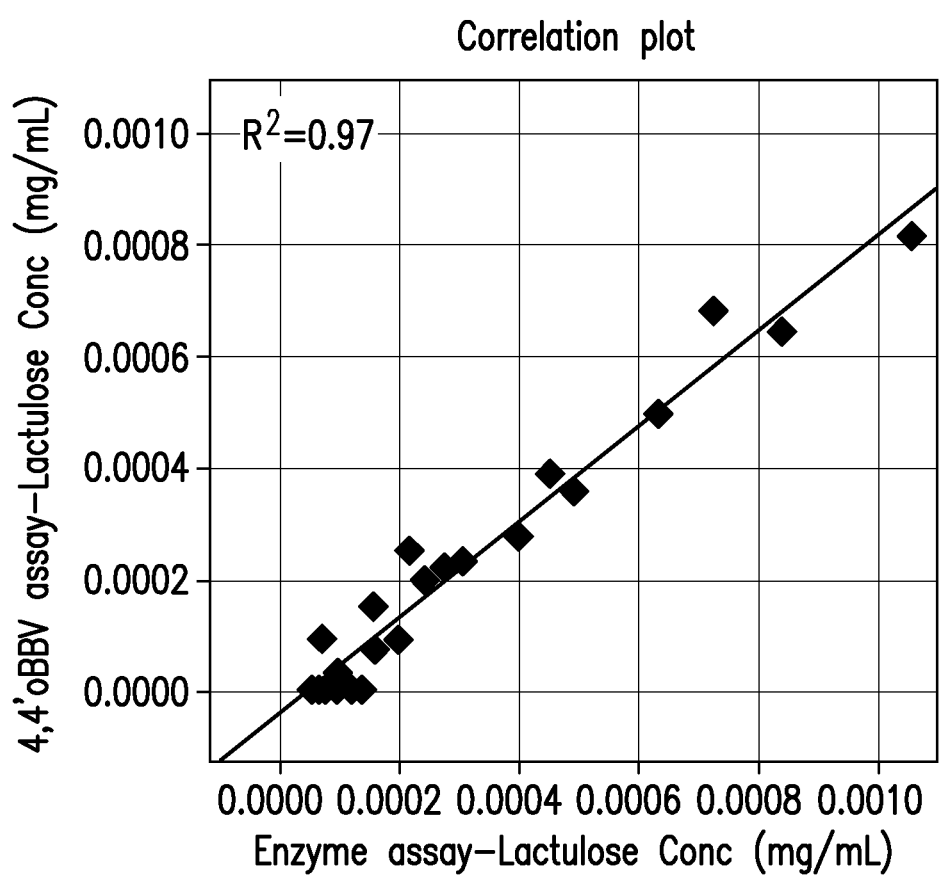
FIG. 5 illustrates correlation between the novel 4,4'oBBV fluorescence lactulose assay and conventional enzyme assay. Standards and 24 urine samples were processed through both assays. The novel 4,4'oBBV based assay was run in quadruplicates to ensure accurate measurement of sample CVs, which was 12% for this dataset. The enzyme assay was run in duplicates with a CV of 8%.

Lactulose and the lactulose/riboflavin ratio: For lactulose measured in human volunteers using 4,4'oBBV for the time interval 0-6 hours, the percent ingested was 0.566±0.252 (mean±SEM) and the lactulose/riboflavin ratio was 0.120±0.092. The sample size in this example was 8 volunteers. The enzyme assay, regarded as a golden standard for urine lactulose, yielded similar results: 0.765±0.216 and 0.103±0.034. Hence, the viologen assay was competitive with the golden standard enzyme assay. The correlation plot shown in FIG. 5 further illustrated the ability of the 4,4'oBBV based fluorescence assay to quantify urine lactulose with results comparable to the established enzymatic assay. The sample size for this assay was 24 urine samples.

What is claimed is:

1. A method of quantifying a sugar in a biological sample collected from a subject, the method comprising:
    contacting a first solution containing a biological sample collected from a subject with an organoboronic compound coupled to a fluorophore, thereby creating a first mixture; wherein the subject has ingested riboflavin and one or both of lactulose or mannitol between 0 and 24 hours prior to collection of the sample;
    measuring a fluorescence emission of the first mixture;
    normalizing the fluorescence emission of the first mixture against a fluorescence emission of the riboflavin in the first mixture and quantifying a sugar in the biological sample collected from the subject using the normalized fluorescence emission of the first mixture.

2. The method of claim 1, wherein the organoboronic compound comprises an organoboronic acid.

3. The method of claim 2, wherein the organoboronic acid comprises a boronic acid viologen.

4. The method of claim 3, wherein the boronic acid viologen is 1,1'-bis(2-boronobenzyl)-4,4'-bipyridinium (4,4'oBBV) or 1-(2-boronobenzyl)-1'-benzyl-4,4'-bipyridinium (4,4'oMBV).

5. The method of claim 1 where the biological sample comprises urine.

6. The method of claim 1, wherein two or more biological samples are collected in the 0 and 24 hours after the ingestion of the riboflavin and one or both of the lactulose or mannitol by the subject.

* * * * *